United States Patent [19]
Simmermon et al.

[11] Patent Number: 5,616,827
[45] Date of Patent: Apr. 1, 1997

[54] FLOW MANIFOLD FOR HIGH PURITY ANALYZERS

[75] Inventors: John C. Simmermon, Newark; Curtis G. Dell, North Star; Douglas Peterson, Newark; Colin B. Blakemore, Hockessin, all of Del.; John B. Remaley, Marcus Hook, Pa.; Anatoly Golod, Wilmington; Robert S. Bear, Jr., Newark, both of Del.

[73] Assignee: Ametek, Inc., Newark, Del.

[21] Appl. No.: 490,640

[22] Filed: Jun. 15, 1995

[51] Int. Cl.⁶ .................................................. G01N 7/00
[52] U.S. Cl. ........................................ 73/29.01; 73/864.81
[58] Field of Search ............................. 73/29.01, 863.31, 73/863.33, 864.81, 864.85

[56] References Cited

U.S. PATENT DOCUMENTS

| | | | |
|---|---|---|---|
| 2,830,945 | 4/1958 | Keidel | 204/195 |
| 3,001,918 | 9/1961 | Czuha, Jr. | 204/1 |
| 3,327,519 | 6/1967 | Crawford | 73/23 |
| 3,329,004 | 7/1967 | King, Jr. | 73/23 |
| 3,511,080 | 5/1970 | Roof | 73/864.81 |
| 3,800,593 | 4/1974 | Bradley | 73/864.81 |
| 5,010,776 | 4/1991 | Lucero et al. | 73/863.23 |
| 5,198,094 | 3/1993 | Mettes | 204/430 |
| 5,259,233 | 11/1993 | Brandt | 73/1 G |
| 5,343,735 | 9/1994 | Succi et al. | 73/29.01 |
| 5,351,120 | 9/1994 | Jurcik et al. | 356/246 |
| 5,379,629 | 1/1995 | Müller | 73/23.42 |

*Primary Examiner*—Hezron E. Williams
*Assistant Examiner*—Jay L. Politzer
*Attorney, Agent, or Firm*—Webb Ziesenheim Bruening

[57] ABSTRACT

A flow manifold for high purity analyzers is described, in which all flow control valving is positioned downstream of the measurement device. Specifically, this new flow manifold is applied to a high purity moisture analyzer that utilizes a quartz crystal microbalance detector. The proposed flow design eliminates outgassing and contamination from upstream valving, deadlegs in the flow path, and significantly improves instrument response speed. Experimental data is provided to confirm the performance advantage of the new manifold design over existing designs.

38 Claims, 5 Drawing Sheets

FLOW MANIFOLD FOR HIGH PURITY ANALYZERS

BACKGROUND OF THE INVENTION

1. Field of the Invention

The present invention is directed generally to an improved flow manifold for analytical equipment which analyzes flowing liquid or gas, where avoidance of contamination of the sample flow from flow control valves, outgassing and valve path deadlegs upstream of the measurement cell are desired. The present invention is more specifically directed to an improved flow manifold for high purity moisture analyzers for ultra-high purity gases.

2. Description of the Prior Art

The performance of moisture analyzers developed for the analysis of high purity gases is significantly affected by quality of the surfaces in all sample wetted parts. Not only do all sample wetted surfaces have to be dried, prior to operation of the analyzer, but the surfaces must also have low affinity for sorbing water from the sample stream. While these characteristics are well known to those skilled in the art of moisture analyzer technology, surface effects of the sample wetted parts have become a major issue in the development of moisture analyzers designed to measure water vapor concentrations in the low parts-per-billion by volume (ppbv) range.

One of the most common components of any sample analysis system is a valve, and it is extremely difficult to find valves that can be easily dried adequately for use in a ppbv moisture detection system. Further, valves are a source of moisture retention and subsequent outgassing. Outgassing is defined as the emission of sorbed or occluded materials or gases. In the sample analysis system of a conventional moisture analyzer (hereafter referred to as a flow manifold) sample flow control valving is located upstream (prior to) a measuring device which is generally a measurement cell. These sample flow control valves are used to alternate the flow of sample gas, reference gas, and calibration gas into the measurement device. Valving that is located upstream of the measurement cell can have a profound impact on instrument performance, due to outgassing. In many cases the level of moisture outgassing observed from a sample valve is much greater than the moisture concentration in the sample gas that is being analyzed. In addition to outgassing, most sample systems that incorporate valves upstream of the measurement cell create "deadlegs" when the sample flow is closed off. Deadlegs are areas in the sample flow where the flow of the sample is retarded for a period of time, as when flow control valves are closed. Deadlegs are to be avoided as they provide a source of moisture retention and subsequent outgassing. Further, deadlegs that are exposed to a moisture laden sample will provide a source of moisture buildup that will be released as a surge upon resumption of the sample flow, seriously compromising the accuracy of any measurement of the moisture content of the sample.

Thus, a need exists in the art for moisture analyzers designed to measure moisture in the low ppbv range which can minimize the effects caused by valves and deadlegs located upstream of the measurement cell.

SUMMARY OF THE INVENTION

It is an object of the present invention to provide flow manifold wherein the flow control valves are removed from upstream of the measurement cell, and wherein the flow control valves are located in a position downstream of the measurement cell. By moving the sample flow control valves downstream of the measurement cell, measurement interferences caused by moisture outgassing from the valves can be completely eliminated.

The present invention comprises a flow manifold for an analytical apparatus which analyzes flowing sample material, the flow manifold including an inlet, an outlet, a sample leg wherein a sample material flows in a sample flow path, a reference leg wherein a reference material flows in a reference flow path, a measurement cell in fluid communication with the sample leg and the reference leg, wherein at least one of the sample material and the reference material flows through the measurement cell. The measurement cell provides an analysis of the sample material versus the reference material. The present invention also includes a sample flow control valve downstream of the flow of the reference material through the measurement cell and a reference flow control valve downstream of the flow of the sample material through the measurement cell, wherein the sample flow path and the reference flow path contain no deadlegs between the inlet and the measurement cell. In this way, contamination of the sample material from the sample flow control valve, the reference flow control valve, and flow path deadlegs upstream of said measurement cell is avoided.

DETAILED DESCRIPTION OF THE PREFERRED EMBODIMENTS

Figure 1:
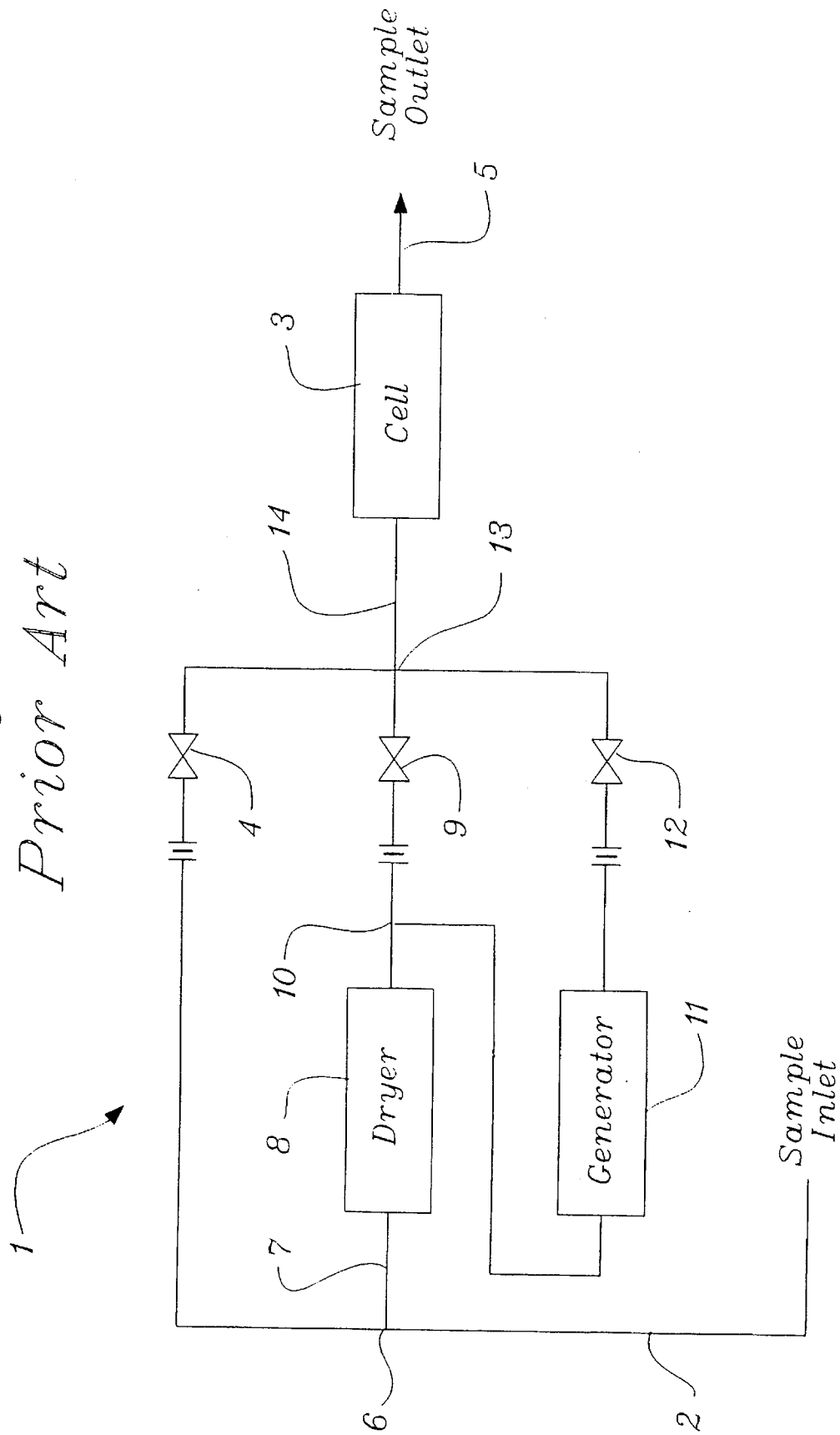
FIG. 1 is a schematic drawing of a flow manifold of a high purity analyzer of the prior art showing placement of flow control valving upstream of the measurement cell.

Referring now to FIG. 1, a flow manifold 1 of a high purity analyzer of the prior art is shown. Typically, a sample gas is introduced into sample leg 2, and the flow of the sample gas into a measurement cell 3 is controlled via sample flow control valve 4. After analysis in the cell 3, the sample gas exits cell 3 via exhaust leg 5. A portion of the sample gas is diverted by fitting 6 to form reference leg 7. The sample gas flows through dryer 8 to dry the sample gas in order to provide a reference for the measurement of the moisture in the sample gas stream. The flow of the reference gas into measurement cell 3 is controlled via reference flow control valve 9. After analysis in the cell 3, the reference gas exits cell 3 via exhaust leg 5. A portion of reference gas is diverted by fitting 10 to a moisture generator 11. Moisture generator 11 is used to supply a desired degree of moisture to the reference gas to calibrate and test the cell 3. Flow of the reference gas into cell 3 is controlled by reference flow control valve 12. In at least one embodiment, the output of sample flow control valve 4 and reference flow control valves 9 and 12 are joined at fitting 13 to provide a single input 14 into cell 3.

In the flow control valve arrangement depicted in FIG. 1, the valves 4, 9 and 12 are a source of moisture retention and subsequent outgassing. In addition, deadlegs are created when valves 4, 9 and 12, respectively, are closed.

Figure 2:
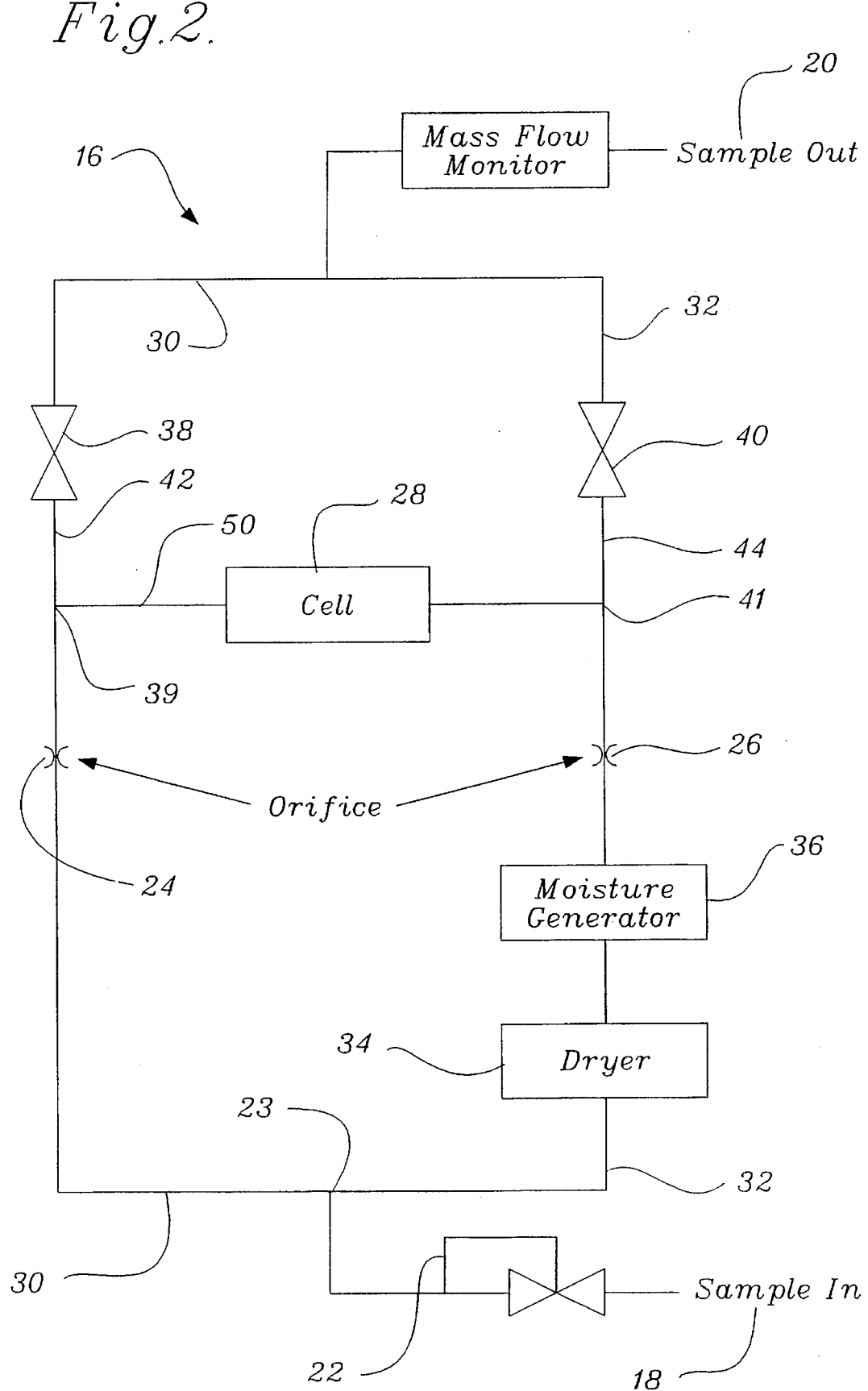
FIG. 2 is a schematic drawing of the flow manifold of the present invention showing placement of the flow control valving downstream of the measurement cell and showing an H-flow manifold analyzer.

FIG. 2 is directed to the flow manifold 16 of the present invention. The present invention is particularly well suited for a moisture analyzer designed for ultra-high purity gases where the water vapor concentrations are in the low parts per billion (ppbv) region. As a result, all of the descriptions and data presented are specific to this type of moisture analyzer. However, it is to be understood that the H-flow manifold which forms the principal concern of this invention may be used in combination with any other types of analyzers where the avoidance of contamination of the sample and reference flows from flow control valving and path flow deadlegs is desired, including other moisture measurement technologies (i.e., electrolytic cells) and other analyzer applications (i.e., non-moisture analyzers).

A diagram of the H-flow manifold 16 of the present invention is shown in FIG. 2. The sample inlet 18 to the analyzer is shown at the bottom of the flow diagram, and the outlet 20 is located at the top of the figure. A pressure regulator 22 is located just past the sample inlet 18. This regulator 22, in conjunction with the precision orifices 24 and 26 located just prior to the measurement cell 28, is used to provide a means of controlling the sample flow into the analyzer and to the measurement cell 28. While pressure regulator 22 could be used alone to control sample flow, for most analyzers this would result in too great a flow of the sample gas. Orifices 24 and 26 function to restrict flow therethrough, thereby permitting a much lower sample flow. In addition, as orifices 24 and 26 are much smaller than the tubing of the flow path, a back pressure is created between pressure regulator 22 and orifices 24 and 26. This back pressure results in a constant pressure at orifices 24 and 26, thereby absorbing any pressure spikes or drops which may occur in the flow path.

The measurement technology employed in the cell 28 is preferably a quartz crystal microbalance (hereinafter "QCM") that has been coated with a polymeric coating, which is well suited to the selective sorption of water molecules. QCM cells are described in U.S. Pat. Nos. 3,260,104 to King, 3,266,291 to King, 3,327,519 to Crawford, 3,427,864 to King and 3,677,066 to King et al., wherein the method of using such cells, including the use of alternating sample and reference streams, are also described.

Immediately following the pressure regulator 22, the gas flow is split by fitting 23, with a first portion of the gas flow going to the sample leg 30 (shown on the left-hand side of the flow diagram) and with a second portion of the flow diverted to the reference leg 32 (shown on the right-hand side of the drawing). In the following discussion it will be assumed that the portions are equal and thus each portion contains one-half of the original flow, but it is to be understood that other ratios are contemplated as within the scope of the present invention.

Located in the reference leg 32 of the analyzer are a sample dryer 34 and a moisture generator 36. The function of the dryer 34 is to dry the sample gas in order to provide a reference stream having a constant level of moisture, against which can be measured the moisture in the sample gas. While the reference stream could be dried to nearly zero ppbv water content, such a dry reference gas stream negatively affects the polymeric coating on the QCM and significantly shortens the usable life of the QCM. In order for the polymeric coating, and hence the QCM, to last as long as possible, it is preferred not to dry the sample gas completely when creating the reference stream, but rather to either: 1) dry it only to a certain point at which it remains slightly "wet"; or 2) to dry it nearly completely but reintroduce a set moisture level with moisture generator 36, as explained in detail below. Thus in one embodiment of the present invention, the moisture generator 36 is not present, and the reference stream is provided by drying the sample gas to a desired level, allowing it to remain slightly "wet", typically containing a moisture concentration in the range of 10 to 20 ppbv. In an alternative embodiment of the present invention, both the dryer 34 and the moisture generator 36 are present as shown in FIG. 2, whereupon the sample gas is dried to a point beyond being "wet" whereupon the moisture generator 36 reintroduces moisture to a desired range, as detailed below. This embodiment is preferred because moisture generator 36 can also be used to calibrate the analyzer by supplying the reference stream with desired moisture levels. While FIG. 1 shows the use of moisture generators in the prior art, it should be noted that the flow manifolds of the prior art required separate valving for such moisture generators, and further, such valving was located upstream of the measurement cell and included deadlegs which the present invention avoids. Finally, in an embodiment not shown in the figures, it should be noted that where the sample being analyzed includes other analyzer applications that are non-moisture analyzers, both dryer 34 and moisture generator 36 may be omitted from reference leg 32, but the benefits associated with flow control valves downstream of the measurement cell or device and the benefits associated with the lack of deadlegs would be retained. This would encompass, for example, analysis of liquid samples versus gaseous samples.

In an alternative embodiment not shown, a separate dry reference gas could be introduced in reference leg 32.

Moisture generator 36 functions as follows. Within moisture generator 36 is a permeation tube, which is a small sealed Teflon® tube that contains a small amount of liquid phase water, which is designed to emit water vapor through the Teflon® barrier at a temperature-dependent rate. The temperature of the moisture generator 36 is controlled, using a precision temperature control circuit. By controlling the temperature of the moisture generator 36, the concentration of water in the reference stream can be precisely maintained. Further, by adjusting the temperature of the moisture generator 36 it is possible to cause precise changes in the moisture concentration of the reference stream. These changes in the moisture output of the moisture generator 36 can be used to calibrate the response of the QCM cell as described above.

When the analyzer is in operation, the temperature of the moisture generator 36 is maintained at a desired value to cause the rate of water emission from the permeation tube to provide a reference stream with a desired level of moisture concentration. Hence, the QCM compares the sample gas to the "wet" reference stream. Under typical conditions the concentration of water vapor present in the reference stream is on the order of 10 to 20 ppbv, and is user selectable both within and outside that range. As in prior art QCM moisture analyzers, the preferred measurement methodology employs alternating or switching the flow of both sample and reference gases to the measurement cell 28. The analytic signal is then taken as the difference in the crystal resonance frequency measured for the sample and reference gases.

The method of switching the gas flows to alternate between the sample and reference streams is the focus of the H-flow manifold of the present invention. Specifically, the location of the flow control valving is responsible for the enhancement in measurement performance of the present invention.

As shown in FIG. 2, the sample flow control valve 38 is positioned downstream of the measurement cell 28 in sample leg 30. Further, a reference flow control valve 40 is similarly positioned downstream of the measurement cell 28 in reference leg 32. A measurement cell conduit 50 extends between and is in flow communication with the sample leg 30 and the reference leg 32. The measurement cell 28 is positioned along the measurement cell conduit 50.

To flow the sample gas through the measurement cell 28, the valve 38 on the sample leg 30 is closed, while the valve 40 on the reference leg 32 is opened. Closing the valve 38 on the sample leg 30 forces the flow of the sample gas through a fitting 39 into the measurement cell conduit 50, through the measurement cell 28 and into the reference leg 32 of the system, where it is exhausted through the opened valve 40.

Conversely, the valve operation can be reversed so that the valve 38 in the sample leg 30 is open and the valve 40 in the reference leg 32 is closed. In this second valving configuration, the flow of reference gas is diverted through fitting 41 into the measurement cell conduit 50, through the measurement cell 28, into the sample leg 30 and is exhausted through the open sample flow control valve 38.

Thus, the sample and reference gases are both continuously flowing through their respective portions of the system, irrespective of which gas stream is being delivered to the measurement cell. There are no "deadlegs" upstream of the measurement cell 28. If the flow diagram of FIG. 2 is interpreted literally, there are two small deadlegs 42 and 44 located between valves 38 and 40 and fittings 39 and 41, respectively. These potential deadlegs 42 and 44 are adjacent to, but are not directly in the flow path. Using a short timing cycle will prevent this from becoming a significant factor. Further, if bleed ports are installed at the valves 38 and 40, the potential deadlegs 42 and 44 are completely eliminated.

EXPERIMENTAL RESULTS

The performance advantages of the H-flow manifold over the conventional upstream valving are illustrated through two sets of experimental results. It should be noted that for all of the data reported here, both a conventional design and an H-flow manifold analyzer were run in parallel. A common calibrator manifold was used to supply the sample gas for both analyzers, and all data were recorded simultaneously from the two analyzer designs. The two analyzers were identical, except for the plumbing of the two flow paths.

EXPERIMENT 1

Figure 3A:
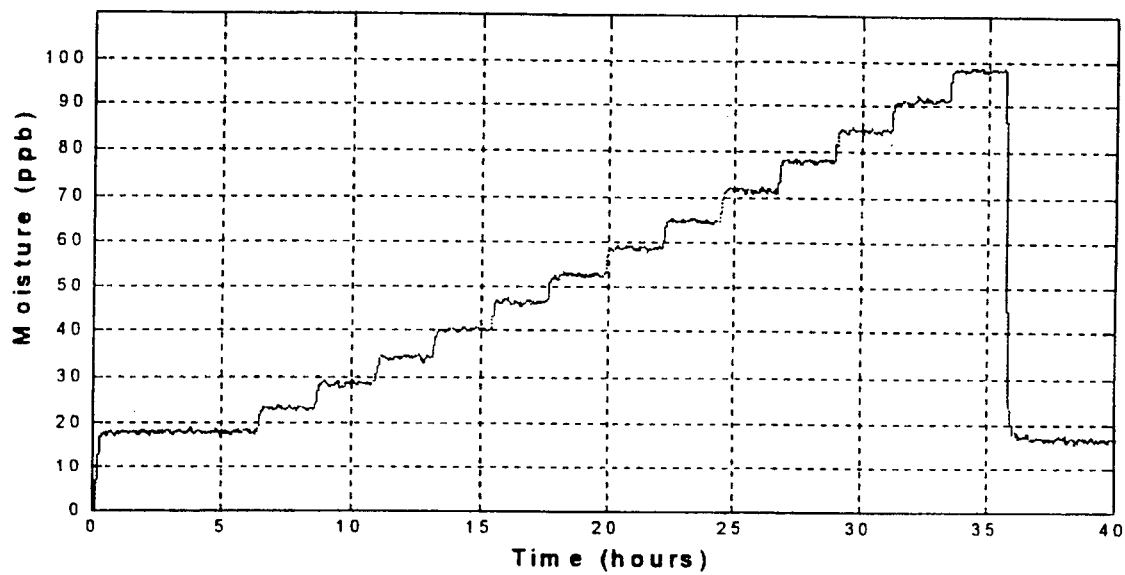
FIG. 3 is a graphic comparison of the response of a prior art analyzer and the H-flow manifold analyzer of the present invention.
Figure 3B:
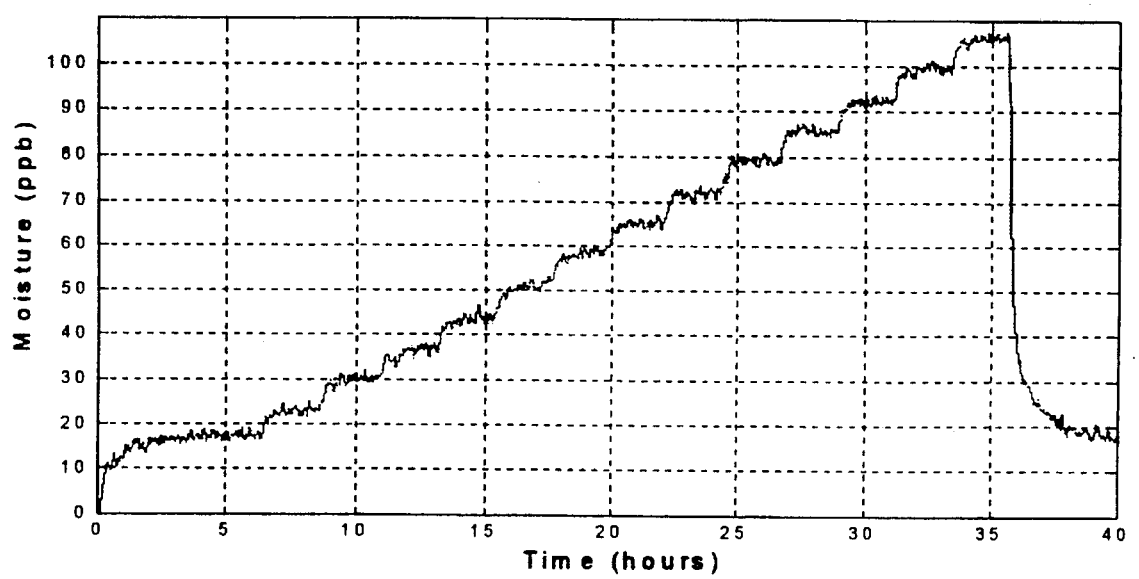

In the first experiment the concentration of moisture in a sample gas was increased in a monotonic series of discrete steps; this type of concentration profile is best described as a "staircase". The responses measured for the H-flow manifold of the present invention are shown in FIG. 3A. The responses measured for the prior art manifold are shown in FIG. 3B. In the response recorded for the H-flow manifold in FIG. 3A, each step in the series of concentration increases is clearly delineated. However, in the response recorded for the conventional analyzer manifold in FIG. 3B, many of the step changes in concentration have been "blurred" due to slow response characteristics of the analyzer.

Even though the concentration changes were small, and a period of two hours was given per water vapor concentration level, a significant performance advantage was observed for the present invention in terms of a much more rapid response time with very little blurring of each step.

EXPERIMENT 2

Figure 4A:
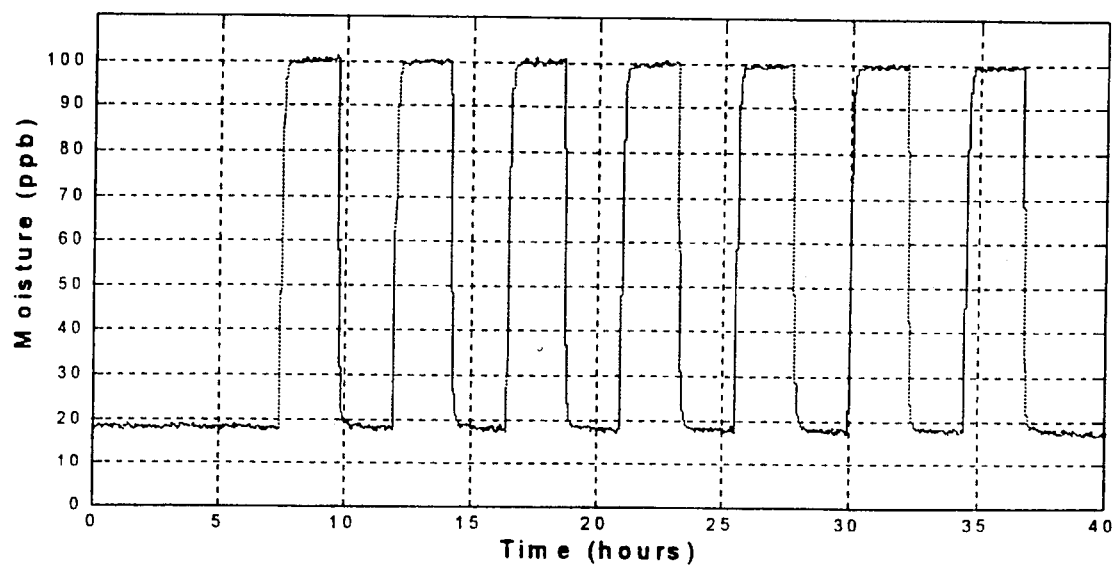
FIG. 4 is a graphic comparison of the response of a prior art analyzer and the H-flow manifold analyzer of the present invention with a repetitive step change in the moisture concentration profile.
Figure 4B:
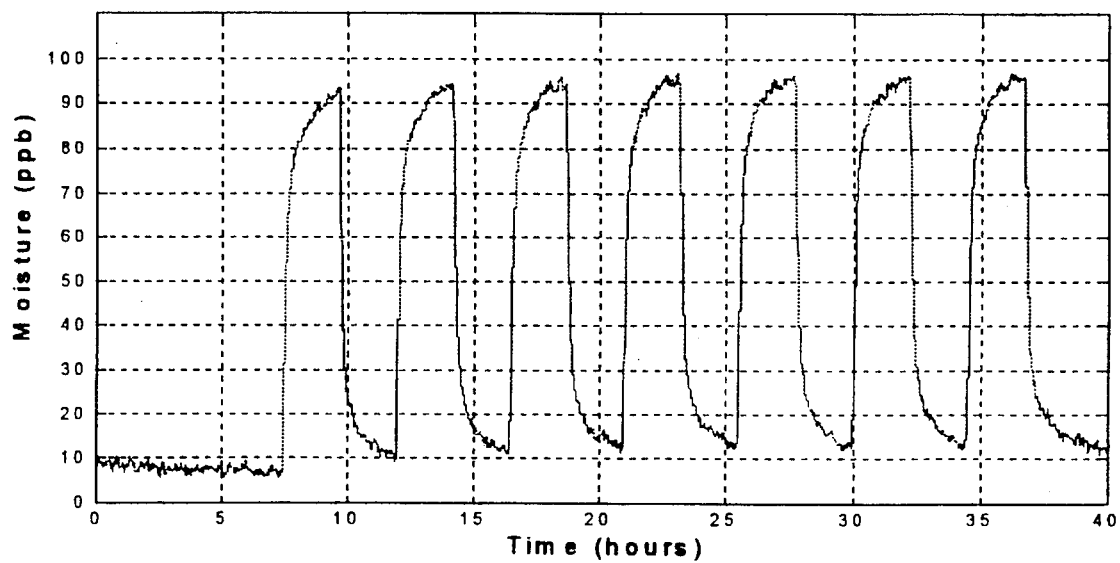

For the second set of experiments, both the conventional analyzer and the H-flow manifold analyzer of the present invention were challenged with a repetitive set of step changes in the moisture concentration profile. In FIG. 4A, the responses recorded the H-flow manifold of the present invention are shown. In FIG. 4B, the responses for the conventional analyzer design are shown. The performance differences between the two designs are pronounced. The H-flow manifold analyzer of the present invention as shown in FIG. 4A recorded a response that tracked the square-wave moisture concentration profile. However, the conventional design was unable to reach a constant output during the duration of each concentration step. This response lag observed for the conventional analyzer flow design, was attributed to moisture retention in the upstream valving and deadlegs.

Figure 5A:
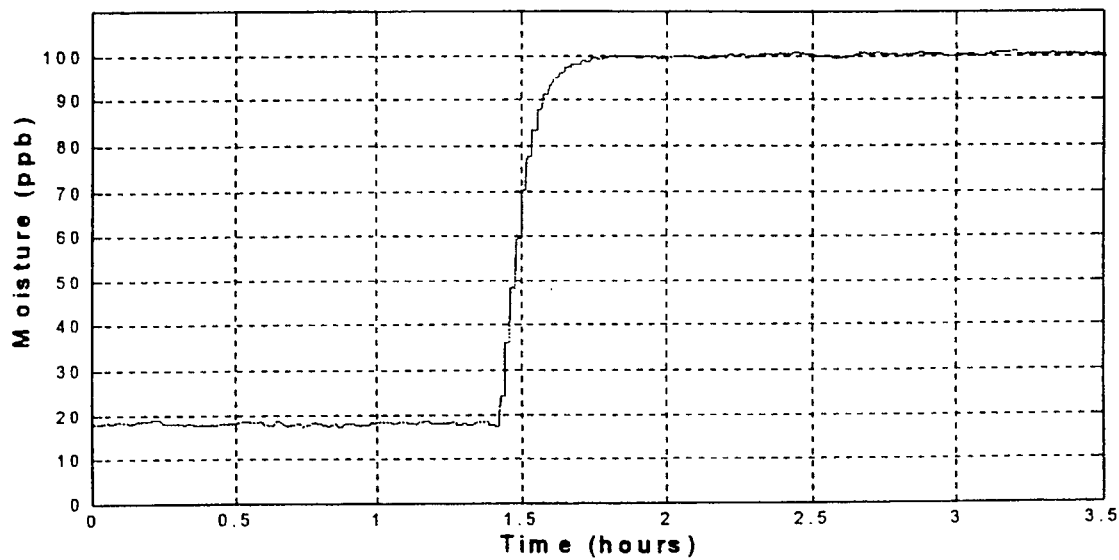
FIG. 5 is an expanded view of the data shown in FIG. 4.
Figure 5B:
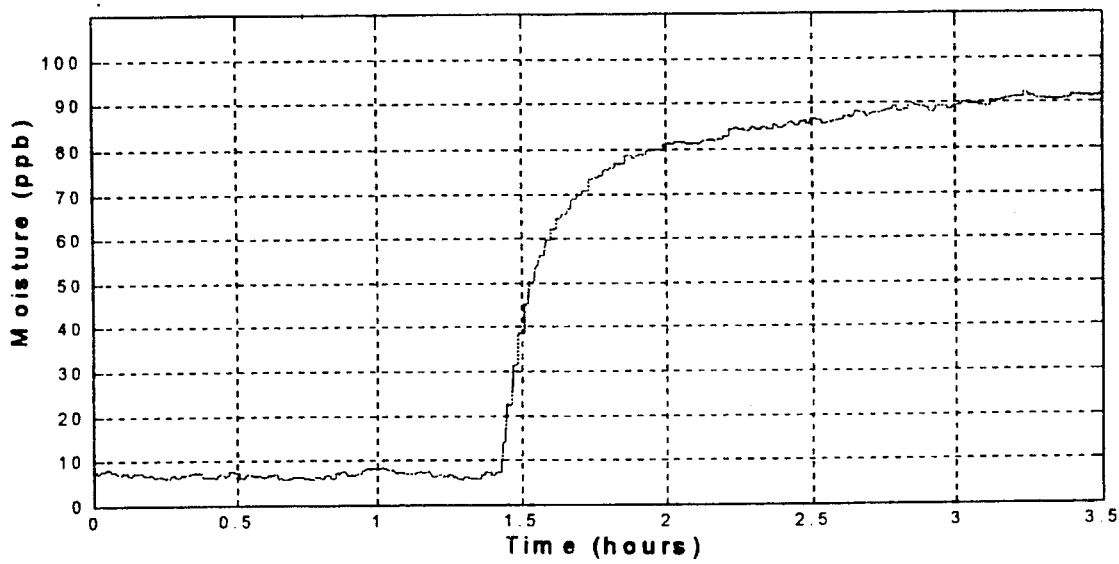

FIG. 5A shows an expanded view of the first concentration jump in the second experiment for the analyzer incorporating the H-flow manifold of the present invention. FIG. 5B shows an expanded view for the first concentration jump in the second experiment for the conventional analyzer of the prior art. It should be noted that the time index has been changed for visual clarity. From a comparison of FIGS. 5A and 5B, it is evident that the H-flow manifold of the present invention reached a 100% response change in less than 15 minutes, while the conventional design was unable to reach a 100% response change within the two-hour period. By 100% response change, it is meant that where the concentration level changes from one concentration level to another, the analyzer has fully stabilized at the new concentration level. This is significant because it assures the user of the present invention that a final concentration value will be attained in a short period. The inventors have found that the present invention is capable of an 80% response to a step change in the water vapor concentration of 10 ppb in the sample material within a 10-minute interval.

Based on these data, it is clear that the present invention represents a significant enhancement in moisture analyzer performance for systems designed to measure in the low ppb region. The proposed flow design eliminates outgassing and contamination from upstream valving, deadlegs in the flow path, and significantly improves instrument response speed.

Having described the preferred embodiments of the present invention, it is to be understood that it may otherwise be embodied within the scope of the appended claims.

We claim:

1. A flow manifold for an analytical apparatus which analyzes flowing sample material, said flow manifold comprising:

a) an inlet;

b) an outlet;

c) a sample leg in flow communication with said inlet and said outlet, wherein a sample material flows in a sample flow path;

d) a reference leg in flow communication with said inlet and said outlet, wherein a reference material flows in a reference flow path;

e) a measurement cell conduit extending between and in flow communication with said sample leg and said reference leg;

f) a measurement cell positioned along said measurement cell conduit and in fluid communication with said sample leg and said reference leg, wherein at least one of said sample material and said reference material flow through said measurement cell, said measurement cell providing an analysis of said sample material versus said reference material;

g) a sample flow control valve located in said sample leg between said measurement cell and said outlet; and h) a reference flow control valve located in said reference leg between said measurement cell and said outlet, wherein said sample flow path and said reference flow path contain no dead legs between said inlet and said measurement cell.

2. The flow manifold of claim 1 wherein said sample material is a gas.

3. The flow manifold of claim 1 wherein said sample material is a liquid.

4. The flow manifold of claim 1 wherein said reference material is a gas.

5. The flow manifold of claim 4 wherein the water vapor concentration in said gas is approximately 10 to 20 ppbv.

6. The flow manifold of claim 1 wherein said reference material is a liquid.

7. The flow manifold of claim 1 further comprising:

a) a pressure regulator;

b) a first orifice located within said sample leg between said inlet and said measurement cell, wherein said first orifice restricts flow through said sample leg; and c) a second orifice located within said reference leg between said inlet and said measurement cell, wherein said second orifice restricts flow through said reference leg.

8. The flow manifold of claim 1 further comprising:

a) a fitting located downstream of said inlet and upstream of said reference leg, said fitting being capable of diverting at least a portion of said sample material into said reference leg; and b) a dryer located within said reference leg downstream of said fitting and upstream of said measurement cell, said dryer drying a portion of said sample material to provide a reference stream in said reference leg.

9. The flow manifold of claim 8 further comprising a moisture generator located within said reference leg upstream of said measurement cell.

10. The flow manifold of claim 9 wherein said moisture generator further comprises a permeation tube containing a small amount of liquid phase water, wherein said moisture generator emits water vapor at a temperature dependent rate.

11. The flow manifold of claim 10 further comprising a precision temperature control circuit to control the temperature of the moisture generator permeation tube, and therefore the rate at which said moisture generator emits water vapor.

12. The flow manifold of claim 11 wherein a concentration of water vapor in said reference stream is user selectable.

13. The flow manifold of claim 12 wherein a concentration of water vapor in said reference stream is 10 to 20 ppbv.

14. The flow manifold of claim 1 wherein said measurement cell is a quartz crystal microbalance.

15. The flow manifold of claim 14 wherein said quartz crystal microbalance further includes a polymeric coating thereon, said coating formulated for selective sorption of water molecules.

16. The flow manifold of claim 1 wherein a 100% response of the measurement cell analysis output to a step change in a water vapor concentration in said sample material occurs in less than 15 minutes.

17. The flow manifold of claim 1 wherein an 80% response of the measurement cell analysis output to a step change in a water vapor concentration of 10 ppbv in said sample material is obtained within a 10 minute interval.

18. The flow manifold as claimed in claim 1 wherein said reference leg is substantially parallel to said sample leg and said measurement cell conduit is substantially perpendicular to said reference leg and said sample leg.

19. A flow manifold for an analytical apparatus which analyzes flowing sample material, said flow manifold comprising:

a) a sample inlet to introduce a sample material into said apparatus;

b) a first fitting downstream of said sample inlet, said first fitting in fluid communication with said sample inlet and positioned to split said flow of said sample material into a first portion and a second portion, said first portion flowing through a sample leg and said second portion flowing through a reference leg;

c) a measurement cell conduit extending between and in flow communication with said sample leg and said reference leg;

d) a measurement cell positioned along said measurement cell conduit and in flow communication with said sample leg and said reference leg;

e) a second fitting downstream of said first fitting and located within said sample leg, said second fitting in fluid communication with said first fitting and positioned to accept said first portion of said sample material, said second fitting positioned to direct said first portion of said sample material alternatively to said measurement cell or to a first flow control valve;

f) a third fitting downstream of said first fitting and located within said reference leg, said third fitting in fluid communication with said first fitting and positioned to accept said second portion of said sample material, said third fitting positioned to direct said second portion of said sample material to said measurement cell or to a second flow control valve;

g) a fourth fitting downstream of and in fluid communication with said first flow control valve and said second flow control valve, said fourth fitting positioned to accept said first portion of said sample material and said second portion of said sample material; and h) a sample outlet downstream of said fourth fitting and in fluid communication with said fourth fitting for discharging said sample material from said apparatus.

20. The flow manifold of claim 19 wherein said sample material is a gas.

21. The flow manifold of claim 19 wherein said sample material is a liquid.

22. The flow manifold of claim 19 wherein said measurement cell is a quartz crystal microbalance.

23. The flow manifold of claim 22 wherein said quartz crystal microbalance is coated with a polymeric coating for selective sorption of water molecules.

24. The flow manifold of claim 19 further comprising:

a) a pressure regulator downstream of said sample inlet, said pressure regulator in fluid communication with said sample inlet;

b) a first orifice located within said sample leg and upstream of said second fitting, wherein said first orifice restricts flow through said sample leg; and c) a second orifice located within said reference leg and upstream of said third fitting, wherein said second orifice restricts flow through said reference leg;

whereupon said pressure regulator and said first and second orifice regulate said flow of said sample material within said flow manifold.

25. The flow manifold of claim 19 further comprising a dryer downstream of said first fitting and located within reference leg, said dryer in fluid communication with said first fitting and being interposed between said first fitting and said third fitting, said dryer drying said second portion of said sample material to a desired level to provide a reference gas stream with a constant water vapor concentration.

26. The flow manifold of claim 25 wherein a concentration of water vapor in said reference gas stream is 10 to 20 ppbv.

27. The flow manifold of claim 25 wherein a concentration of water vapor in said reference gas stream is selectable by a user of said flow manifold.

28. The flow manifold of claim 25 further comprising a moisture generator downstream of said dryer and located within said reference leg, said moisture generator being in fluid communication with said dryer and being interposed between said dryer and said third fitting.

29. The flow manifold of claim 28 wherein said moisture generator further comprises a permeation tube containing a small amount of liquid phase water, wherein said moisture generator emits water vapor at a temperature dependent rate.

30. The flow manifold of claim 29 further comprising a precision temperature control circuit to control the temperature of the moisture generator permeation tube and therefore the rate at which said moisture generator emits water vapor.

31. The flow manifold of claim 19 wherein a 100% response of the measurement cell analysis output to a step change in a water vapor concentration in said sample material occurs in less than 15 minutes.

32. The flow manifold of claim 19 wherein an 80% response of the measurement cell analysis output to a step change in a water vapor concentration of 10 ppbv in said sample material is obtained within a 10 minute interval.

33. The flow manifold as claimed in claim 19 wherein said reference leg is substantially parallel to said sample leg and said measurement cell conduit is substantially perpendicular to said reference leg and said sample leg.

34. A substantially H-shaped apparatus for measuring the concentration of moisture in a flowing sample material comprising:

a) a sample inlet to introduce a sample material into said apparatus;

b) a pressure regulator downstream of said sample inlet, said pressure regulator in fluid communication with said sample inlet to regulate said flow of said sample material within said apparatus;

c) a first fitting downstream of said pressure regulator, said first fitting in fluid communication with said pressure regulator and positioned to split said flow of said sample material into a first portion and a second portion, said first portion flowing through a sample leg and said second portion flowing through a reference leg;

d) a measurement cell conduit extending between and in flow communication with said sample leg and said reference leg;

e) a measurement cell positioned along said measurement cell conduit;

f) a second fitting downstream of said first fitting and located within said sample leg, said second fitting in fluid communication with said first fitting and positioned to accept said first portion of said sample material, said second fitting positioned to direct said first portion of said sample material alternatively into said measurement cell conduit to said measurement cell or to a first flow control valve;

g) a third fitting downstream of said first fitting and located within said reference leg, said third fitting in fluid communication with said first fitting and positioned to accept said second portion of said sample material, said third fitting positioned to direct said second portion of said sample material into said measurement cell conduit to said measurement cell or to a second flow control valve;

h) a dryer downstream of said first fitting and located within said reference leg, said dryer in fluid communication with said first fitting and being interposed between said first fitting and said third fitting, said dryer drying said second portion of said sample material to a desired level to provide a reference gas stream with a constant water vapor concentration;

i) a moisture generator downstream of said dryer and located within said reference leg, said moisture generator being in fluid communication with said dryer and being interposed between said dryer and said third fitting;

j) a first orifice located within said sample leg and upstream of said second fitting, wherein said first orifice restricts flow through said sample leg;

k) a second orifice located within said reference leg and upstream of said third fitting, wherein said second orifice restricts flow through said reference leg;

l) a fourth fitting downstream of and in fluid communication with said first flow control valve and said second flow control valve, said fourth fitting positioned to accept said first portion of said sample material and said second portion of said sample material; and m) a sample outlet downstream of said fourth fitting and in fluid communication with said fourth fitting for discharging said sample material from said apparatus.

35. The apparatus as claimed in claim 34 wherein said sample leg is substantially parallel to said reference leg and said measurement cell conduit is substantially perpendicular to said sample leg and said reference leg.

36. A method of measuring the concentration of moisture in a flowing sample material comprising the steps of:

a) providing the analytical apparatus of claim 32;

b) introducing a sample material to be analyzed into said apparatus through said sample inlet;

c) adjusting said flow of said gas or fluid to be analyzed through said apparatus to a desired flow rate with said pressure regulator;

d) creating a reference stream by activating said dryer within said reference leg to dry said second portion of said sample material to create said reference stream having a water vapor concentration within a preselected range;

e) flowing said sample material to said measurement cell by closing said first flow control valve and opening said second flow control valve;

f) flowing said reference stream to said measurement cell by closing said second flow control valve and opening said first flow control valve; and g) alternately switching the flow of said sample material and said reference stream to said measurement cell to provide an analytic signal of the water concentration in said sample material which is measured as the difference in a crystal resonance frequency measured for said sample material and for said reference stream.

37. A substantially H-shaped flow manifold for an analytical apparatus which analyzes flowing sample material, said flow manifold comprising:

a sample leg having a sample flow control valve;

a reference leg having a reference flow control valve;

an inlet in flow communication with said sample leg and said reference leg;

an outlet in flow communication with said sample leg and said reference leg;

a measurement cell conduit extending between and in flow communication with said sample leg and said reference leg; and a measurement cell positioned along said measurement cell conduit, wherein said sample flow control valve is located in said sample leg between said measurement cell conduit and said outlet and wherein said reference flow control valve is located in said reference leg between said measurement cell conduit and said outlet.

38. The flow manifold as claimed in claim 37 wherein said sample leg is substantially parallel to said reference leg and said measurement cell conduit is substantially perpendicular to said sample leg and said reference leg.

* * * * *